(12) United States Patent
Maimon et al.

(10) Patent No.: US 11,883,288 B2
(45) Date of Patent: *Jan. 30, 2024

(54) EXPANDABLE SHEATH AND METHODS OF USING THE SAME

(71) Applicant: Edwards Lifesciences Corporation, Irvine, CA (US)

(72) Inventors: David Maimon, Atlit (IL); Eran Goldberg, Nesher (IL); Liron Tayeb, Peduel (IL)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 461 days.

This patent is subject to a terminal disclaimer.

(21) Appl. No.: 17/113,268

(22) Filed: Dec. 7, 2020

(65) Prior Publication Data

US 2021/0085459 A1 Mar. 25, 2021

Related U.S. Application Data

(63) Continuation of application No. 15/636,201, filed on Jun. 28, 2017, now Pat. No. 10,856,981.

(Continued)

(51) Int. Cl.
*A61F 2/24* (2006.01)
*A61M 25/00* (2006.01)
*A61M 25/06* (2006.01)

(52) U.S. Cl.
CPC ....... *A61F 2/2436* (2013.01); *A61M 25/0023* (2013.01); *A61M 25/0662* (2013.01); *A61M 25/005* (2013.01); *A61M 25/0045* (2013.01); *A61M 2025/0024* (2013.01); *A61M 2205/0216* (2013.01); *A61M 2205/0266* (2013.01)

(58) Field of Classification Search
CPC .. A61M 2025/0024; A61M 2205/0216; A61M 2205/0266; A61M 25/0023; A61M 25/0045; A61M 25/005; A61M 25/0662; A61F 2/2436
See application file for complete search history.

(56) References Cited

U.S. PATENT DOCUMENTS 4,035,849 A 7/1977 Angell et al.
4,592,340 A 6/1986 Boyles
(Continued)

FOREIGN PATENT DOCUMENTS

DE 19532846 A1 3/1997
DE 19907646 A1 8/2000
(Continued)

*Primary Examiner* — Brandy S Lee
(74) *Attorney, Agent, or Firm* — Meunier Carlin Curfman LLC; Joel B. German

(57) ABSTRACT

The expandable sheath and methods of use disclosed herein are used to deliver a prosthetic device through a patient's vasculature. The sheath is constructed to be expandable in the circumferential direction, while maintaining sufficient stiffness in the longitudinal direction to withstand pushing and resist kinking. The sheath includes a plurality of curved arms extending outwardly from a longitudinally extending spine. The curved arms move away from the longitudinal axis of the sheath when pushed radially outwardly by a passing prosthetic device, and move back toward the longitudinal axis once the prosthetic device has passed.

20 Claims, 21 Drawing Sheets

Related U.S. Application Data

(60) Provisional application No. 62/475,759, filed on Mar. 23, 2017, provisional application No. 62/360,162, filed on Jul. 8, 2016.

(56) References Cited

U.S. PATENT DOCUMENTS

| | | | |
|---|---|---|---|
| 4,994,077 A | 2/1991 | Dobben | |
| 5,059,177 A | 10/1991 | Towne et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,639,274 A | 6/1997 | Fischell et al. | |
| 5,728,068 A | 3/1998 | Leone et al. | |
| 5,840,081 A | 11/1998 | Andersen et al. | |
| 5,968,068 A | 10/1999 | Dehdashtian et al. | |
| 6,168,614 B1 | 1/2001 | Andersen et al. | |
| 6,217,585 B1 | 4/2001 | Houser et al. | |
| 6,379,372 B1 | 4/2002 | Dehdashtian et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| 8,449,606 B2 | 5/2013 | Eliasen et al. | |
| 10,856,981 B2 * | 12/2020 | Maimon | A61F 2/2436 |
| 2002/0032481 A1 | 3/2002 | Gabbay | |
| 2003/0050694 A1 | 3/2003 | Yang et al. | |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2007/0005131 A1 | 1/2007 | Taylor | |
| 2007/0203575 A1 | 8/2007 | Forster et al. | |
| 2007/0265700 A1 | 11/2007 | Eliasen et al. | |
| 2008/0125853 A1 | 5/2008 | Bailey et al. | |
| 2008/0294230 A1 | 11/2008 | Parker | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0082000 A1 * | 4/2010 | Honeck | A61M 25/0668 604/246 |
| 2010/0198347 A1 | 8/2010 | Zakay et al. | |
| 2011/0015729 A1 | 1/2011 | Jimenez et al. | |
| 2011/0245909 A1 | 10/2011 | Schmid et al. | |
| 2012/0123529 A1 | 5/2012 | Levi et al. | |
| 2013/0281787 A1 | 10/2013 | Avneri et al. | |
| 2013/0317598 A1 | 11/2013 | Rowe et al. | |
| 2016/0296332 A1 * | 10/2016 | Zhou | A61F 2/2427 |

FOREIGN PATENT DOCUMENTS

| | | |
|---|---|---|
| EP | 0592410 B1 | 10/1995 |
| EP | 0850607 A1 | 7/1998 |
| EP | 1796597 A2 | 6/2007 |
| FR | 2815844 A1 | 5/2002 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

* cited by examiner

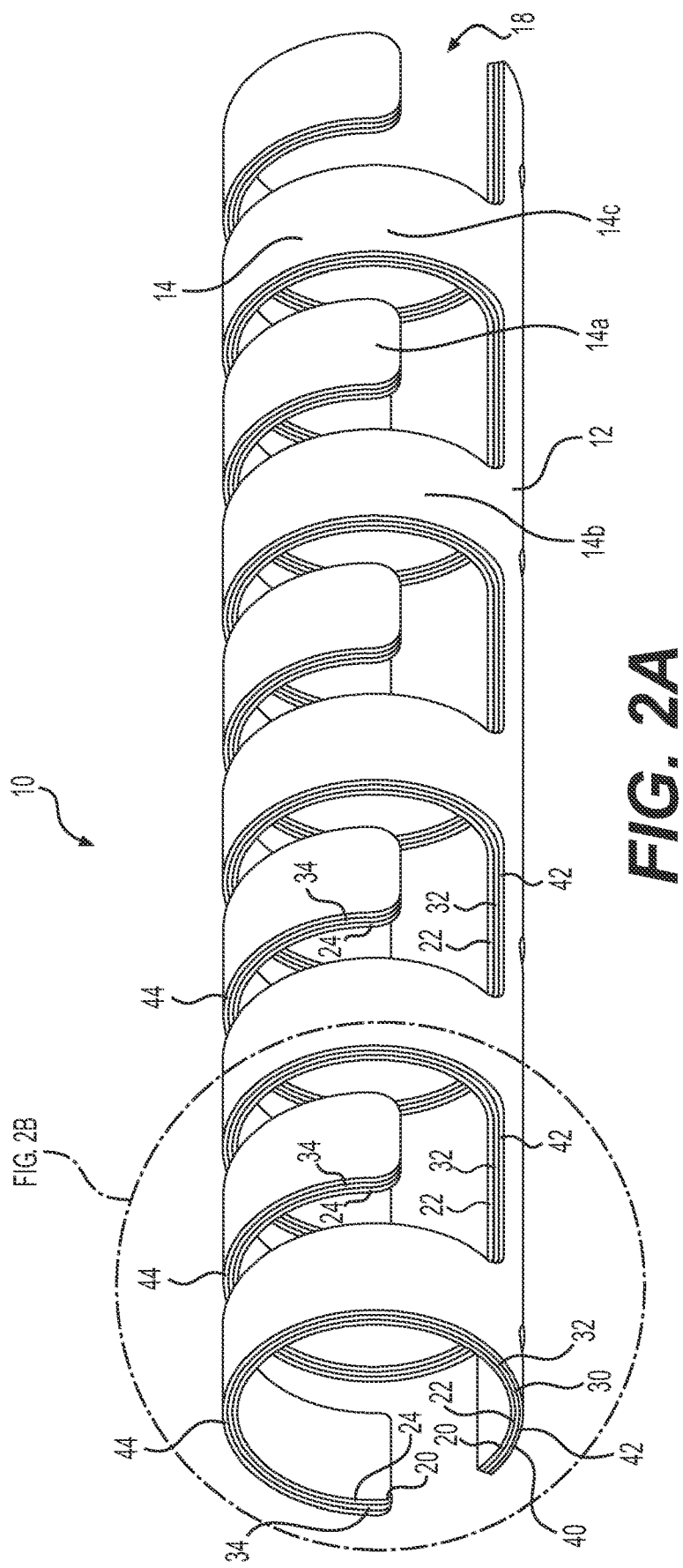

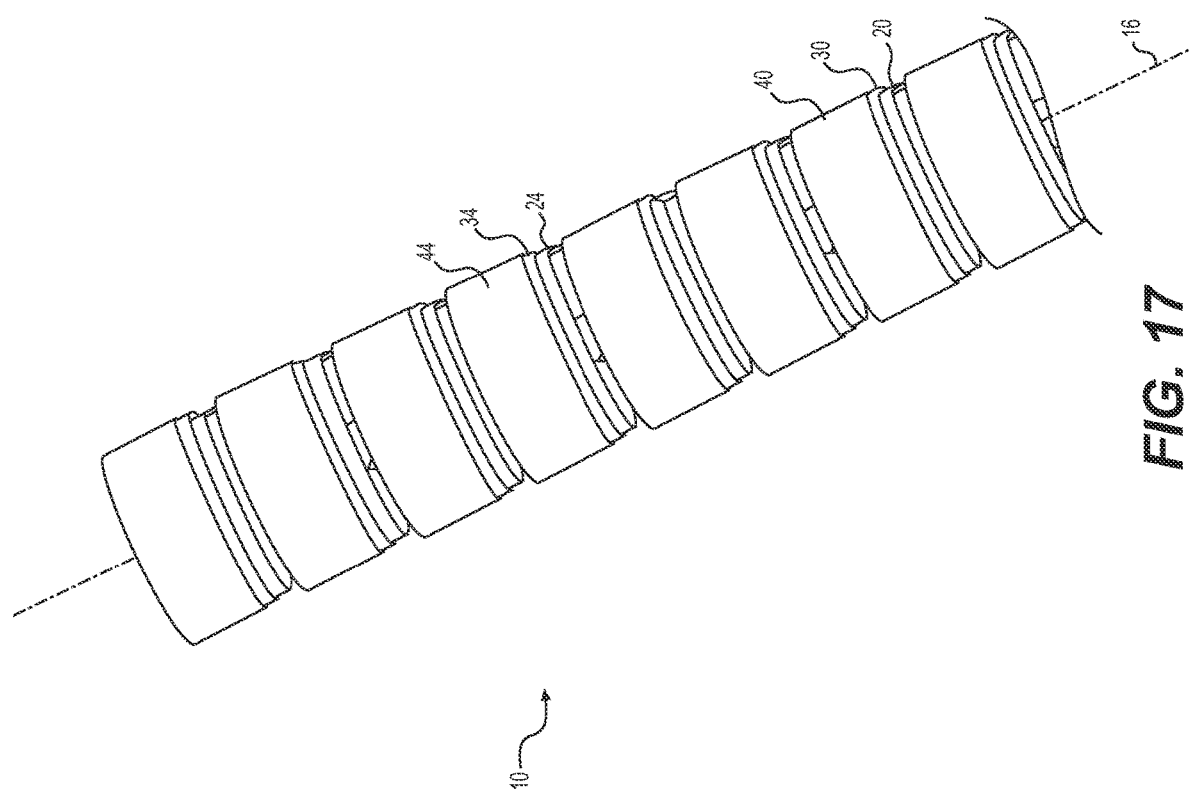

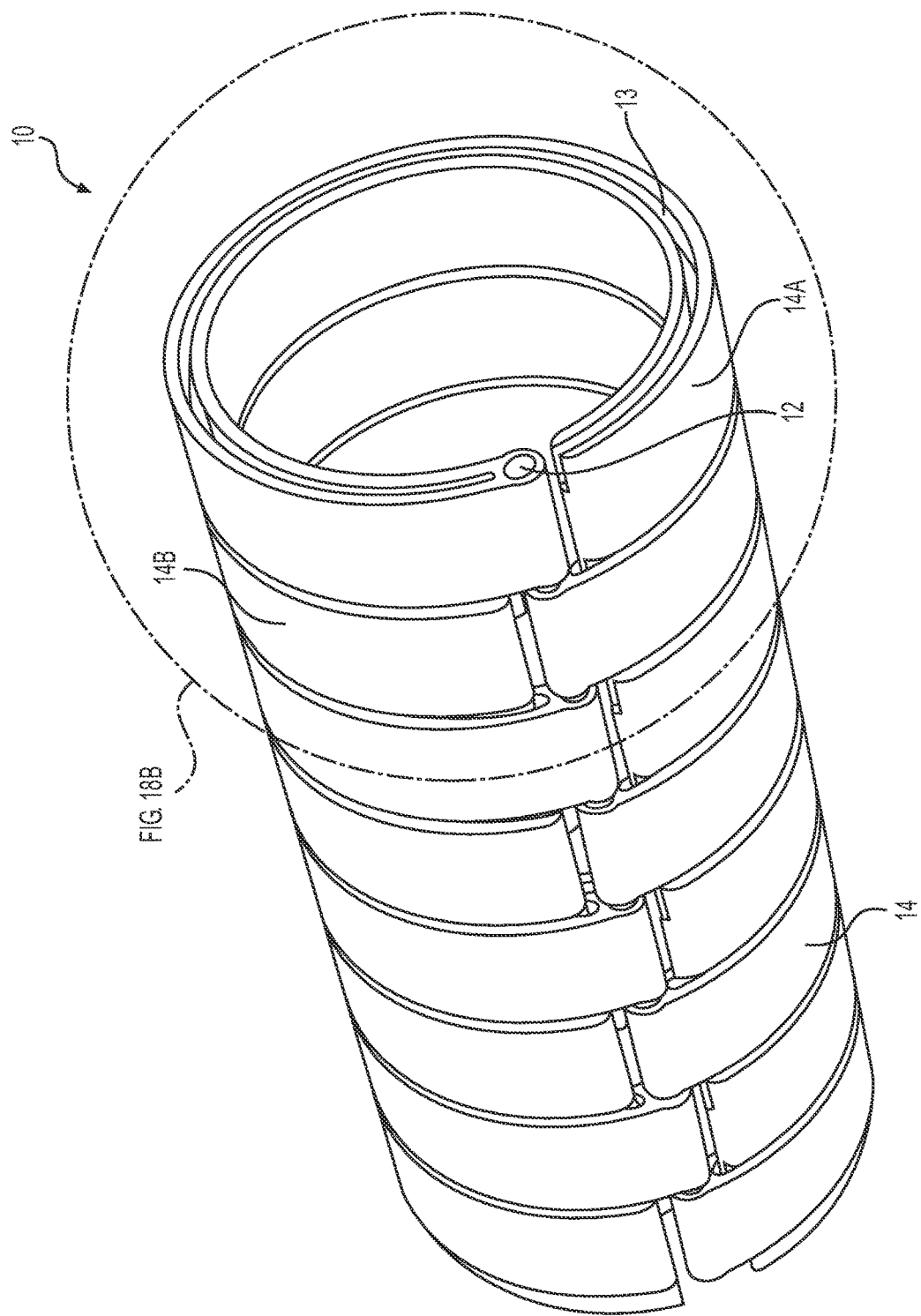

EXPANDABLE SHEATH AND METHODS OF USING THE SAME

This application is a continuation of U.S. application Ser. No. 15/636,201, filed Jun. 28, 2017 (issued as U.S. Pat. No. 10,856,981), which claims the benefit of U.S. Provisional Patent Application Ser. No. 62/360,162 filed on Jul. 8, 2016, entitled EXPANDABLE SHEATH AND METHODS OF USING THE SAME, and U.S. Provisional Patent Application Ser. No. 62/475,759 filed Mar. 23, 2017, entitled EXPANDABLE SHEATH AND METHODS OF USING THE SAME, the disclosures of which are hereby incorporated by reference.

FIELD

The present application concerns embodiments of a sheath for use with catheter-based technologies to introduce a prosthetic device, such as a heart valve or other implant, into the patient's vasculature.

BACKGROUND

Endovascular delivery catheter assemblies are used to implant prosthetic devices, such as a prosthetic heart valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques, including transcatheter delivery methods.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for the prosthetic implant, such as a heart valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths reduce the overall profile of the sheath to reduce risk of damage to the vessel. Such sheaths tend to have complex mechanisms, such as ratcheting mechanisms that maintain the shaft or sheath in an expanded configuration once a device with a larger diameter than the sheaths original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque. The addition of radially expanding properties can also hinder a practitioner's ability to push the sheath without it bending or kinking. Thus, there remains a need for further improvements in introducer sheaths for endovascular systems used for implanting heart valves and other prosthetic devices.

SUMMARY

A radially expandable introducer sheath should offer flexibility, strength, and resiliency upon expansion in the radial direction, while retaining a balance of strength and bendability along the longitudinal axis. The expandable sheath disclosed herein is constructed to be highly expandable and collapsible in the circumferential direction, while maintaining sufficient stiffness in the longitudinal direction to withstand pushing and limit kinking. The sheath includes two or more layers of curved arms extending outwardly from two or more layered, longitudinally extending spines. The layers of curved arms are configured to slide against each other in the circumferential direction, while longitudinal motion between the layers is restricted. The curved arms are elastically resilient, such that they move away from the longitudinal axis of the sheath when pushed outward by a passing prosthetic device, and move back toward the longitudinal axis once the prosthetic device has passed. The use of multiple layers of curved arms, as opposed to one layer at an equivalent thickness, provides enhanced flexibility in the radial direction without sacrificing strength.

Disclosed herein are expandable sheaths for introducing prosthetic devices into the vasculature of a patient. The expandable sheaths include a first layer and at least one additional layer positioned around the first layer. Longitudinal motion is restricted between the first layer and the additional layer. The first and additional layers include first and additional longitudinally extending spines. The first and additional layers also include first and additional pluralities of curved arms, which are attached to and extend away from the longitudinally extending spines. The pluralities of curved arms extend around the longitudinal axis in a circumferential direction so as to at least partially define a longitudinally extending lumen. The pluralities of curved arms are elastically resilient and configured to move away from the longitudinal axis when exposed to a radially outwardly directed force and to move back toward the longitudinal axis upon release of the force. The additional plurality of curved arms at least partially overlays the first plurality of curved arms, and is configured to slide circumferentially along the first plurality of curved arms. In some embodiments, the additional plurality of curved arms fully overlays the first plurality of curved arms. In some embodiments, the first layer and the additional layer each comprise nitinol.

Some embodiments include a third layer. The first, second and third layers can each have a thickness of from 0.04-0.1 millimeters measured in a radial direction, such that a total thickness of a sheath wall is from 0.12 to 0.3 millimeters. For example, the first, second and third layers could each have a thickness of from 0.05 millimeters measured in a radial direction, such that the total thickness of the sheath wall is 0.15 millimeters.

In some embodiments, the curved arms extend from the longitudinally extending spine in alternating directions moving along the longitudinal axis for both the first plurality of curved arms and for the additional plurality of curved arms. Each curved arm extends circumferentially more than 270-degrees around the longitudinal axis. In some embodiments, each curved arm extends at a right angle from a side of the longitudinally extending spine supporting the curved arm.

In some embodiments, the curved arms extend from the longitudinally extending spines in pairs moving along the longitudinal axis. Each curved arm extends between 90 and 180 degrees circumferentially around the longitudinal axis.

In some embodiments, the first and additional longitudinally extending spines are circumferentially spaced from each other. For example, the first and additional longitudinally extending spines can be circumferentially spaced from each other by about 180-degrees.

The first longitudinally extending spine and the additional longitudinally extending spine are secured to each other by a fixation mechanism. In some embodiments, the fixation mechanism is a suture extending through at least one hole defined in the first longitudinally extending spine and at least one hole defined in the additional longitudinally extending spine. In some embodiments, the fixation mechanism comprises a rivet or a bonding agent. In some embodiments, the fixation mechanism comprises an elastic polymer tubing at least partially encapsulating the first and additional layers.

In another embodiment, the expandable sheath can include a plurality of curved arms. The plurality of curved arms include a first and second curved arm rotationally coupled along a longitudinally extending axis. The plurality of curved arms define a longitudinally extending lumen of the sheath and are movable between an expanded and non-expanded state. The plurality of curved arms move away from a central longitudinal axis of the sheath to the expanded state when exposed to a radially outwardly directed force, and move toward the central longitudinal axis upon release of the force to the non-expanded state In some embodiments, the expandable sheath includes a spine that extends along the longitudinally extending axis, and the first and second curved arms can be rotationally coupled to the spine. The longitudinally extending axis can be offset from the central longitudinal axis of the sheath.

In some embodiments, the first curved arm includes a projection extending from an end surface of the first curved arm. The projection is received within a corresponding opening provided in an end surface of the second curved arm such that the first and second curved arms are rotationally coupled at the projection. Some embodiments include a third curved arm rotationally coupled along the longitudinally extending axis. The second curved arm can include a projection extending from an other end surface of the second curved arm. The projection of the second curved arm can be received within an opening provided in an end surface of the third curved arm such that the second and third curved arms are rotationally coupled at the projection of the second curved arm.

In some embodiments, the first curved arm rotates away from the central longitudinal axis in a first direction towards the expanded state, and the second curved arm rotates away from the central longitudinal axis in a second direction towards the expanded state. Each of the plurality of curved arms extends circumferentially at least 180-degrees around the central longitudinal axis of the sheath.

In some embodiments, the plurality of curved arms slidingly engage during movement between the expanded and non-expanded state. The plurality of curved arms each include a ridge projecting from an end surface of the curved arm and a correspondingly shaped groove provided in an opposite end surface of the curved arm. The first curved arm can include a first groove and the second curved arm can include a corresponding second ridge, where the first groove received within and slidingly engages the second groove when the first and second curved arms are moved between the expanded and non-expanded state. The sheath can include elastic polymer tubing at least partially covering the expandable sheath.

Methods of delivering prosthetic devices are also disclosed herein. The methods include positioning an expandable sheath within the vascular system of a patient, the sheath including a longitudinally extending spine and a plurality of curved arms extending from the spine. As the prosthetic device is moved through a longitudinally extending lumen of the expandable sheath, a portion of the sheath is locally expanded from a non-expanded state to an expanded state by a radially outwardly directed force provided at an inner surface of the sheath by advancement of the device. During expansion of the sheath, the plurality of curved arms move radially outward, away from a longitudinal axis of the sheath and enlarge the diameter of the longitudinally extending lumen. The portion of the sheath is locally contracted from the expanded state at least partially back to the non-expanded state upon passage of the device from that portion of the sheath.

In some methods, the plurality of curved arms includes a first plurality of curved arms and a second plurality of curved arms at least partially layered on the first plurality. Movement of the sheath between the expanded and non-expanded state causes the first plurality of curved arms to slide with respect to the second plurality of curved arms in the circumferential direction.

In some embodiments, the plurality of curved arms includes a first curved arm and a second curved arm each rotatably coupled to the longitudinally extending spine. Movement of the sheath between the expanded and non-expanded state causes the first and second curved arms to rotate with respect to the longitudinally extending spine. Movement of the sheath between the expanded and non-expanded state also causes a ridge extending from the first curved arm to slidingly engage a groove provided in the second curved arm.

DESCRIPTION OF DRAWINGS

FIG. 2A shows a side perspective view of an example expandable sheath including a plurality of curved arms.

FIG. 17 shows a perspective view of an example expandable sheath having longitudinally staggered layers.

FIG. 18A shows a perspective view of an example expandable sheath including a plurality of curved arms that pivot/flex from a common longitudinally extending spine.

DETAILED DESCRIPTION

Figure 1A:
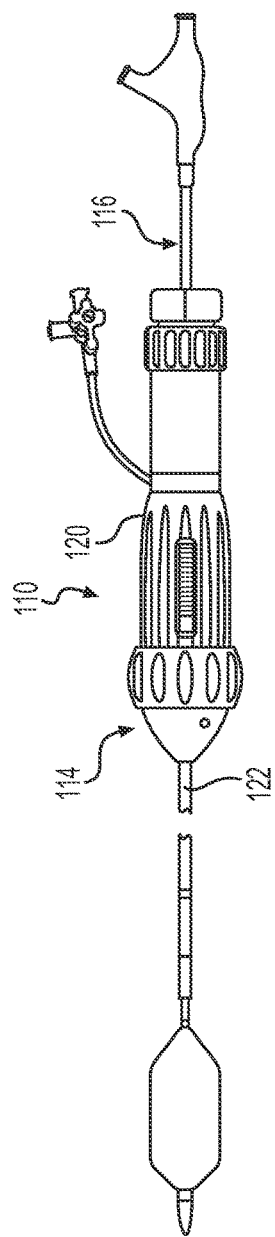
FIGS. 1A-C show a delivery system for a cardiovascular prosthetic device, including an expandable sheath as disclosed herein.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

The expandable introducer sheath disclosed herein is used to deliver a prosthetic device through a patient's vasculature to a procedure site within the body. The sheath is constructed to be highly expandable and collapsible in the circumferential direction, while maintaining sufficient stiffness in the longitudinal direction to withstand pushing and limit kinking. In one embodiment, the expandable introducer sheath includes two or more layers of curved arms extending outwardly from two or more layered, longitudinally extending spines. The layers of curved arms are configured to slide against each other in the circumferential direction, while longitudinal motion between the layers is restricted. The curved arms are elastically resilient, such that they move away from the longitudinal axis of the sheath when pushed radially outwardly by a passing prosthetic device, and move back toward the longitudinal axis once the prosthetic device has passed. The use of multiple layers of curved arms, as opposed to one layer at an equivalent thickness, provides enhanced flexibility in the radial direction without sacrificing strength.

In another embodiment, the expandable introducer sheath can include a series of curved arms that rotate/flex to allow the sheath to expand and contract during delivery of the prosthetic device. The sheath includes a series of curved arms pivotally attached at a common axis/spine. The curved arms can also be constructed from an elastically resilient material, such that as a prosthetic device passes through the sheath, the curved arms pivot and flex away from the spine. The curved arms engage each other to allow for coordinated expansion and to improve push force in the longitudinal direction and limit kinking (engagement/contact between arms helps to maintain longitudinal stiffness of the sheath). Engagement between adjacent curved arms is facilitated by sliding engagement between ridges and grooves provided on opposite ends of adjacent curved arms. Some embodiments can include an elastic polymer tubing covering the curved arms and spine to encourage the curved arms to return back to their original position after the passage of the device.

Figure 1B:
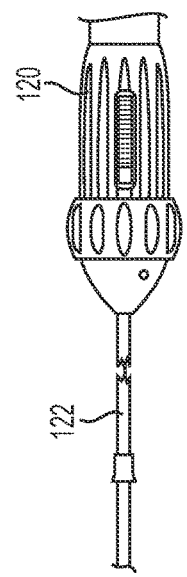
Figure 1C:
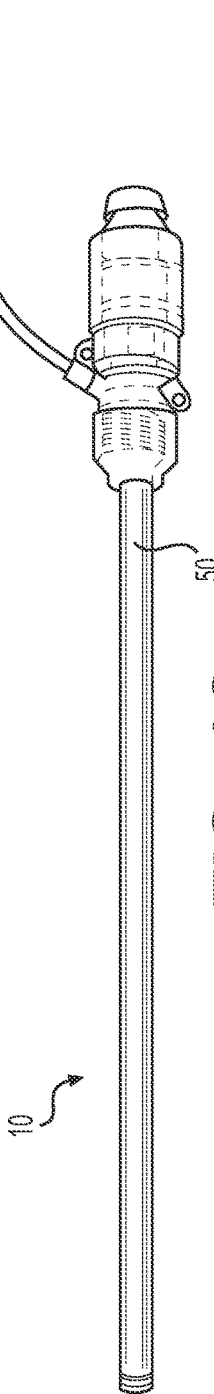

FIGS. 1A-1C illustrate an expandable introducer sheath 10 according to the present disclosure and a representative delivery apparatus 110 for delivering a prosthetic implant, such as a prosthetic heart valve, to a patient. It should be understood that the delivery apparatus 110 described herein is exemplary only, and that other similar delivery systems can of course be used with the expandable sheath 10. The delivery apparatus 110 illustrated herein generally includes a steerable guide catheter 114 and a balloon catheter 116 extending through the guide catheter 114.

The guide catheter 114 and the balloon catheter 116 illustrated in FIGS. 1A-1B are adapted to slide longitudinally relative to each other to facilitate delivery and positioning of prosthetic heart valve at an implantation site in a patient's body, as described in detail below. The guide catheter 114 includes a handle portion 120 and an elongated guide tube, or shaft, 122 extending from handle portion 120 (FIG. 1B).

FIG. 1C illustrates an expandable sheath 10 that is used to introduce the delivery apparatus 110 and the prosthetic device into the patient's body. The expandable sheath 10 has a central lumen to guide passage of the delivery system for the prosthetic heart valve. At a proximal end the expandable sheath 10 includes a hemostasis valve that prevents leakage of pressurized blood. Generally, during use a distal end of the sheath 10 is passed through the skin of the patient and the sheath 10 is inserted into a vessel, such as the femoral artery. The delivery apparatus 110 with its implant is then inserted into the sheath 10 through the hemostasis valve, and advanced through the patient's vasculature where the implant is delivered and implanted within the patient.

Figure 2B:
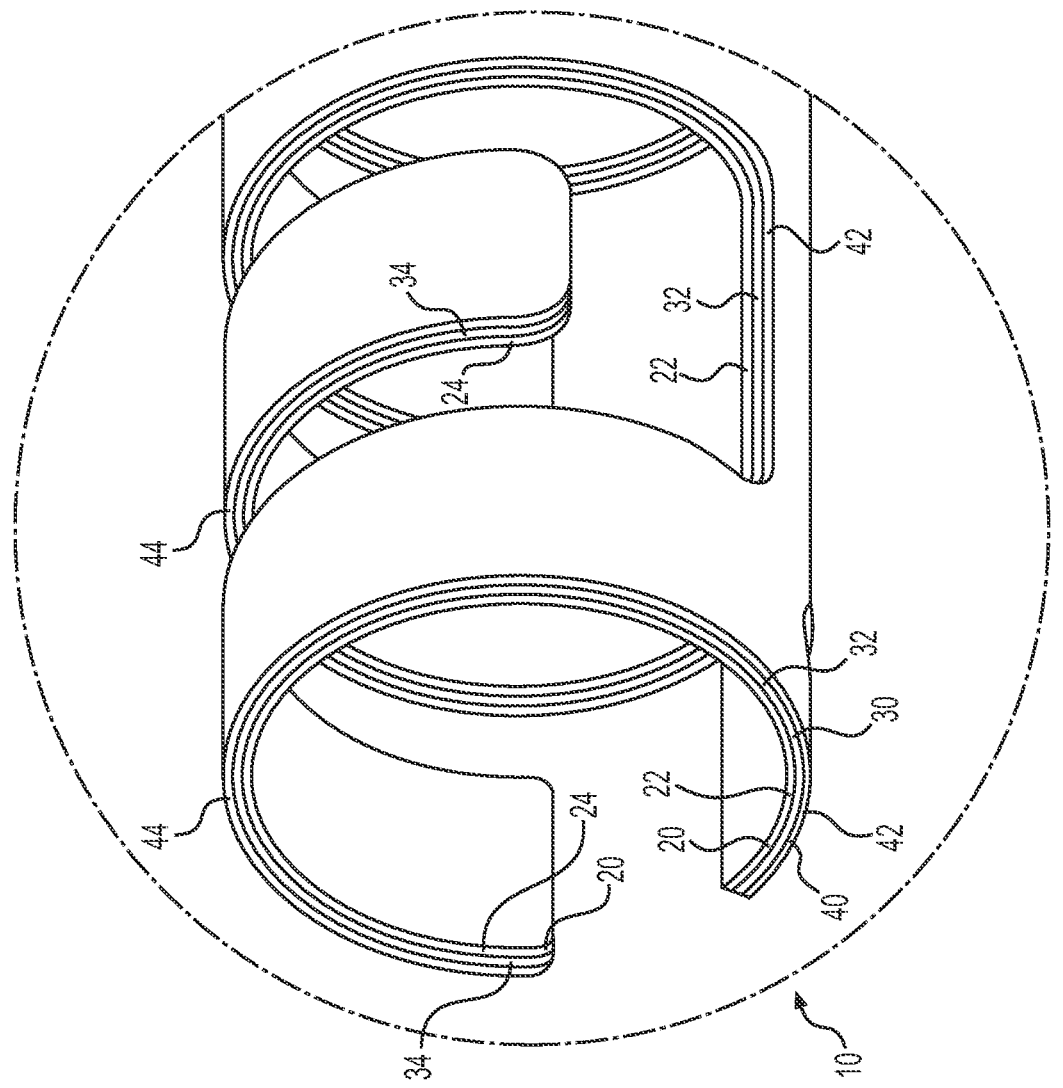
FIG. 2B is a magnified view of a portion of FIG. 2A.
Figure 4:
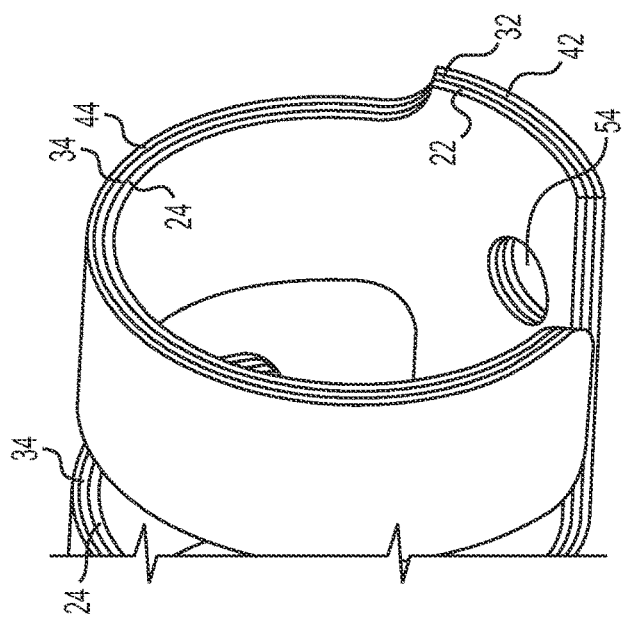
FIG. 4 shows a close up view of one side of the expandable sheath of FIG. 2A.
Figure 6:
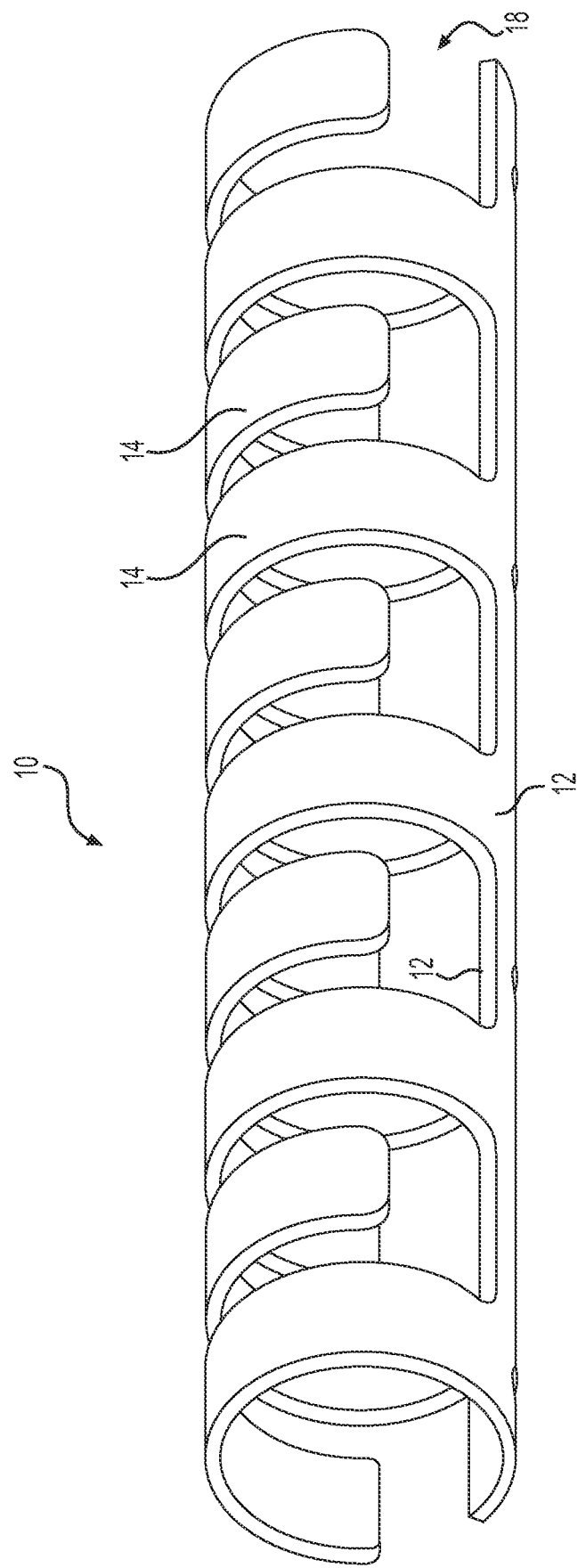
FIG. 6 shows a side perspective view of example single-layered expandable sheath having a plurality of curved arms.

An example expandable sheath 10 is shown in FIG. 2A. An enlarged view of an end of the sheath 10 is provided in FIG. 2B. The sheath 10 includes a longitudinally extending spine 12 having a plurality of curved arms 14 extending alternately from opposite sides of the spine 12. As depicted in FIG. 2A, the opposing curved arms 14 are offset such that the body/length of the curved arm 14a extends between adjacent curved arms 14b, 14c provided on the opposite side of the spine 12. The sheath 10 can be constructed in layers. For example, as illustrated in FIG. 2A, the sheath 10 can include three layers of material defining the spine 12 and curved arms 14. As illustrated in FIG. 2A, the expandable sheath 10 has a first (innermost) layer 20 that includes a first longitudinally extending spine 22 and a first plurality of curved arms 24 attached to the spine 22. An additional, second (middle) layer 30 extends over the outside surface of the first layer 20. The second layer 30 includes an additional, second longitudinally extending spine 32 and an additional, second plurality of curved arms 34. The curved arms 34 of the second layer 30 overlay the curved arms 24 of the first layer 20. The embodiment of FIGS. 2A-B also includes a third (outermost) layer 40 including a third longitudinally extending spine 42 and a third plurality of curved arms 44. The curved arms 44 of the third layer 40 overlay the curved arms 34 of the second layer 30. While three layers are shown in FIGS. 2A-B, it is contemplated that other embodiments could include two, four, or more than four layers. Alternatively, in certain other embodiments of expandable sheath 10 the curved arms 14 and the spine 12 can be formed from only one layer, as shown in example expandable sheath illustrated in FIG. 6.

Figure 3:
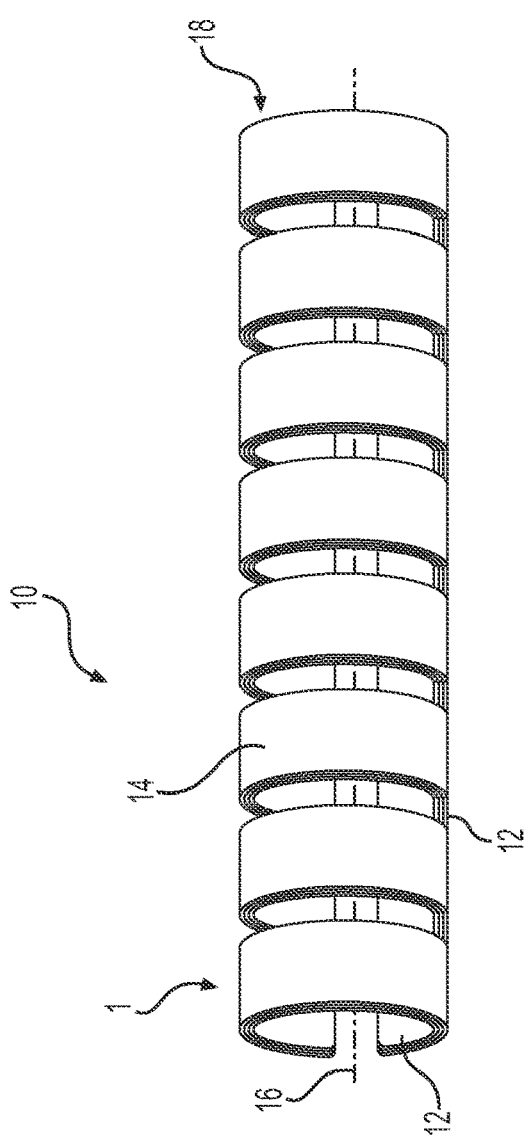
FIG. 3 shows a top perspective view of the expandable sheath of FIG. 2A.

The longitudinally extending spine 12 provides the sheath 10 with stiffness in the longitudinal direction. This stiffness reduces bending or kinking in the longitudinal direction while the sheath 10 is being pushed into the patient's vasculature. Each curved arm 14 is attached to and extends away from the longitudinally extending spine 12 and curves around the longitudinal axis 16 (FIG. 3) of the sheath 10. The spine 12 extends parallel to the longitudinal axis 16. The circumferential curvature of the curved arms 14 around the longitudinal axis 16 at least partially defines a longitudinally extending lumen 18 through which the prosthetic heart valve 122 will pass. The various layers of curved arms 24, 34, 44 are configured to slide along each other in the circumferential direction as the sheath 10/arms 14 move between an expanded and non-expanded condition. This sliding occurs along the (circumferential) length of the curved arms 14 when the sheath 10 expands and contracts as a prosthetic heart valve 122 is pushed through the longitudinally extending lumen 18 of the sheath 10. The curved arms 24, 34, 44 are elastically resilient, moving away from the longitudinal axis 16 when exposed to a radially outwardly directed force (such as the force from a prosthetic heart valve 122 moving through the lumen 18), and then moving back toward the longitudinal axis 16 upon release of the force (for example, once the prosthetic heart valve 122 has passed).

The curved arms 14 of the embodiment shown in FIGS. 2-5 extend from their respective longitudinally extending spine 12 in alternating directions. For example, in FIG. 2A, starting at the distal end (left side of figure), the first set of curved arms 14 circle the longitudinal axis 16 in a first (counterclockwise) direction. Moving towards the proximal end (right side of figure) of the sheath 10 along the longitudinal axis 16, the next set curved arms 14 circle the longitudinal axis 16 in the opposite (clockwise) direction, the next set of curved arms 14 curve back in the first direction, and so on, along the entire length of the sheath 10. Though not shown, it is contemplated that the direction of the curved arms 14 can alternate along the length of the sheath 10 at regular and/or irregular intervals. The curved arms 14 extending in alternating directions along the length of the sheath 10 is advantageous because during expansion, the profile of the sheath 10 stays somewhat circular, a shape well adapted to the shape of the vasculature. Additionally, the passing device is fully encircled by the curved arms 14 during its passage, protecting the vasculature from the passing device. It is also contemplated that all of the curved arms 14 can extend in the same direction along the length of the sheath 10.

The circumferential distance that the curved arms 14 extend around the longitudinal axis 16 can vary by embodiment. The embodiment of FIG. 2A shows the curved arms 14 extending greater than 270-degrees around the longitudinal axis 16, but other embodiments can have curved arms extend to a greater or lesser extent around the longitudinal axis 16. For example, the curved arms 14 could extend greater than 180-degrees, including 190, 200, 210, 220, 230, 240, 250, 260, 270, 280, 290, 300, 310, 320, 340, 350, or greater than 350 degrees up to 360-degrees.

Figure 5:
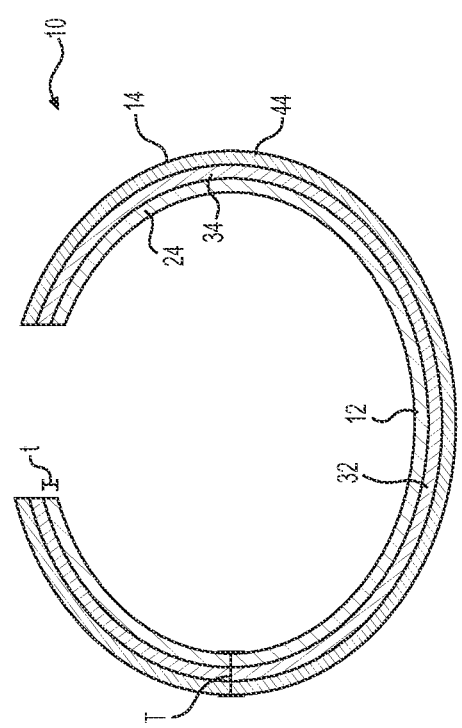
FIG. 5 is a cross section of the example sheath of FIG. 2A.
Figure 20:
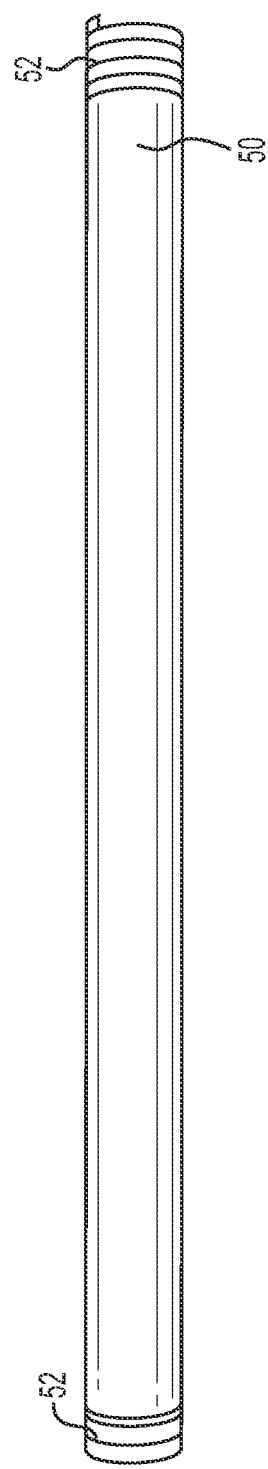
FIG. 20 shows side view of an example expandable sheath where the layers are partially encapsulated in an elastic polymer tubing.

While the various layers of curved arms 24, 34, 44 are configured to slide against each other in the circumferential direction, longitudinal motion of the spines 22, 32, 34 with respect to each other is restricted. In turn, this restricts longitudinal sliding between the layers of the sheath 10 and between the layers of the curved arms 24, 34, 44. In some embodiments, longitudinal motion is limited by a fixation mechanism coupling the layers of the sheath 10 together. The fixation mechanism can include an elastic polymer tubing 50 at least partially encapsulating the layers of the sheath 10, or it could include one or more circumferential rings 52 extending around the outermost layer, as seen in FIGS. 1C and 20 and described in more detail below. Alternatively or in addition, the fixation mechanism can be applied to or between the layered longitudinal spines 12 to prevent longitudinal slippage of the layers with respect to each other. The fixation mechanism could include a mechanical or chemical fastener coupling the layers of the sheath 10 together. For example, the fixation mechanism could include a suture, a rivet, or a bonding agent. In one non-limiting example, the fixation mechanism includes a suture that can be threaded through a bore hole 54 extending through the layered longitudinally extending spines 12, as shown in FIG. 5. The holes 54 through each of the layers 20, 30, 40 are aligned so that the suture can be threaded through each longitudinally extending spine 22, 32, 42. The sheath 10 could also include multiple mechanical and/or chemical fixation mechanisms provided along the length of the spine 12. For example, the sheath 10 could include a suture extending along the spine 12, through a series of suture holes 54, a row of rivets, and/or longitudinally extending strips of bonding agent/adhesive provided between the layered spines 22, 32, 42.

Referring now to FIG. 5, the thickness (t) of an individual layer can be, in some embodiments, from 0.04 to 0.1 millimeters. In embodiments including three layers, the total thickness (T) of the sheath wall is therefore from 0.12 to 0.3 millimeters. In certain embodiments, the thickness of an individual layer is 0.05 millimeters, such that a three layer embodiment has a total sheath wall thickness 29 of 0.15 millimeters.

Figure 7:
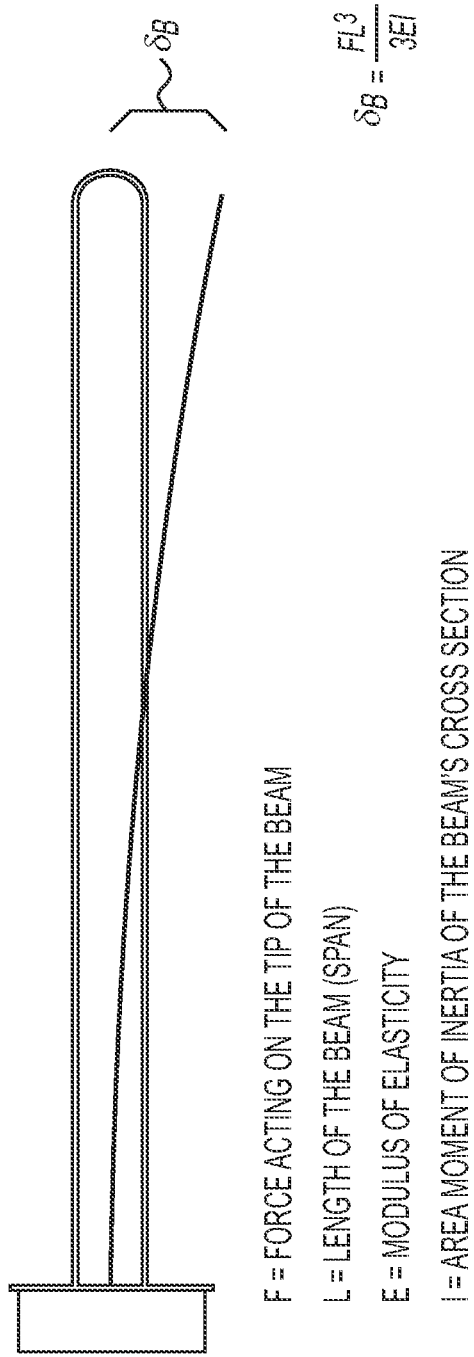
FIG. 7 is a diagram demonstrating the mechanical principles behind the expandable sheath.

The layering of multiple thin curved arms 14 provides certain advantages to an expandable sheath 10. Because each individual layer is constructed from a thin layer of material than if the sheath 10 were constructed from a (thicker) single layer, the individual arms have improved flexibility over a single curved arm having the same overall thickness. The multiple layers of curved arms 14 create a structure similar to a leaf spring. The flexibility of a beam (or curved arm) increases as thinner layers are used according to the formula shown in FIG. 7. However, increased flexibility is accompanied by a decrease in stiffness, such that the individual curved arm 14 is weaker in all directions. The layering of multiple thin curved arms 14 offsets this decrease in stiffness. Because every layer acts separately by slipping on the next one in the circumferential direction, the structure remains relatively stiff, especially in the longitudinal direction, while achieving a high range of deflection.

The shape, number, and spacing between the curved arms 14 can vary. However, while increased spacing between curved arms 14 can provide enhanced bendability, it is at the expense of decreased strength. For example, in contrast to the example sheath 10 of FIGS. 2-6 where there is space between opposing curved arms 14, FIGS. 8-12 illustrate an example sheath 10 having curved arms 14 arranged more closely together and/or in contact. For example, it is contemplated that the opposing curved arms 14 are arranged so there is sliding contact between opposing arms 14 as the sheath 10 expands and contracts. While individual layers are not shown in FIGS. 8-12, it is contemplated that the sheath 10 of FIGS. 8-12 can be a single or multiple layer sheath 10.

Other variable features include the extent of circumferential curvature of the curved arms 14, the width of the longitudinal spine 12, the length of the curved arms 14, the overall inner and outer diameters of the sheath 10, the width of the curved arms 14, and the extent to which individual layers overlap each other in the longitudinal direction. Widening (circumferentially) the longitudinal spine 12 creates a sheath that better withstands pushing and limits kinking. However, the widening of the spine 12 results in a corresponding shortening of the curved arms 14, which determines the maximum diameter the sheath 10 can be opened while keeping the passing implant at least partially contained by the curved arms 14. It is contemplated that the outer diameter of the sheath 10 can vary from 3.3 to 3.8 millimeters in the nonexpanded state, and from 7.5 to 8 millimeters in the expanded state. The individual layers can overlap fully in the longitudinal direction, or they may be shifted from each other by 0.1 to 0.3 millimeters per layer.

Figure 8:
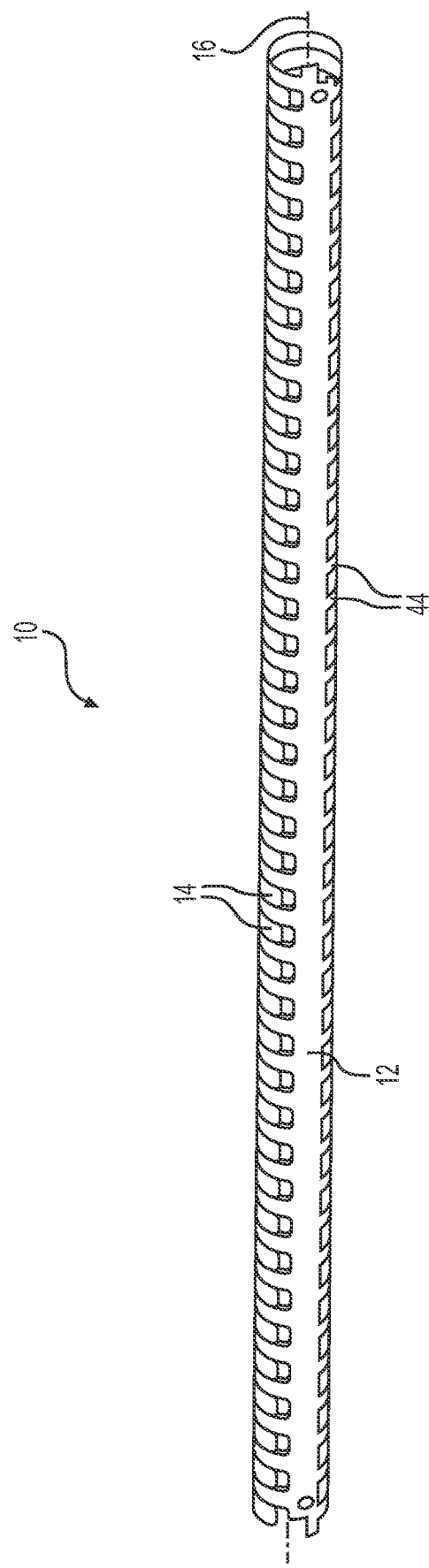
FIG. 8 is a side perspective view of another example expandable sheath.
Figure 9:
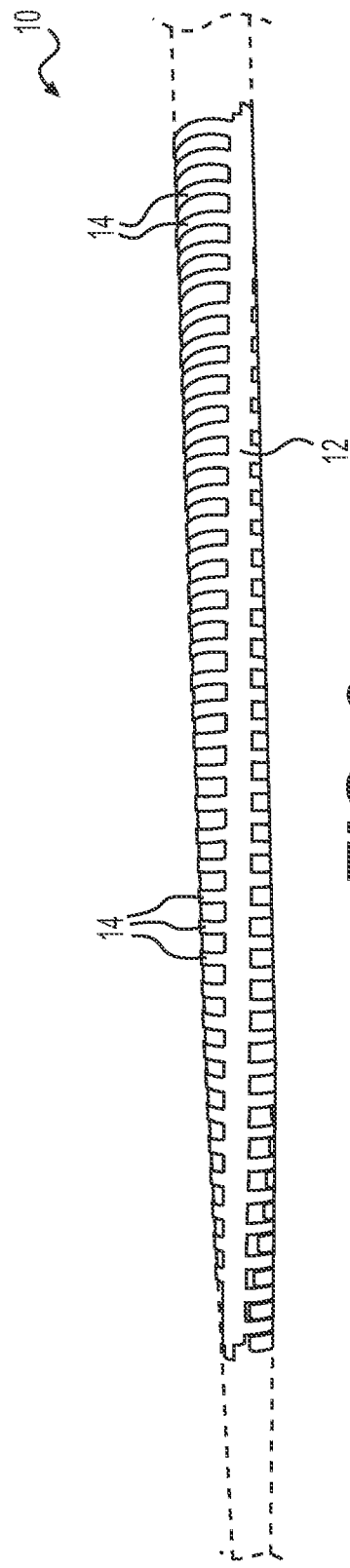
FIGS. 9-11 show the example sheath of FIG. 8 positioned on a dilator to demonstrate the expansion of the curved arms.
Figure 10:
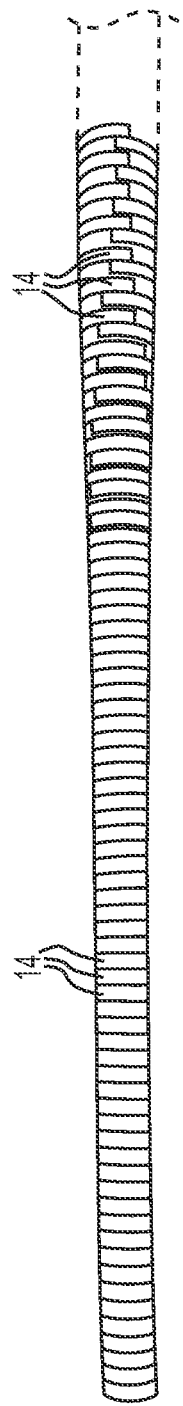
Figure 11:
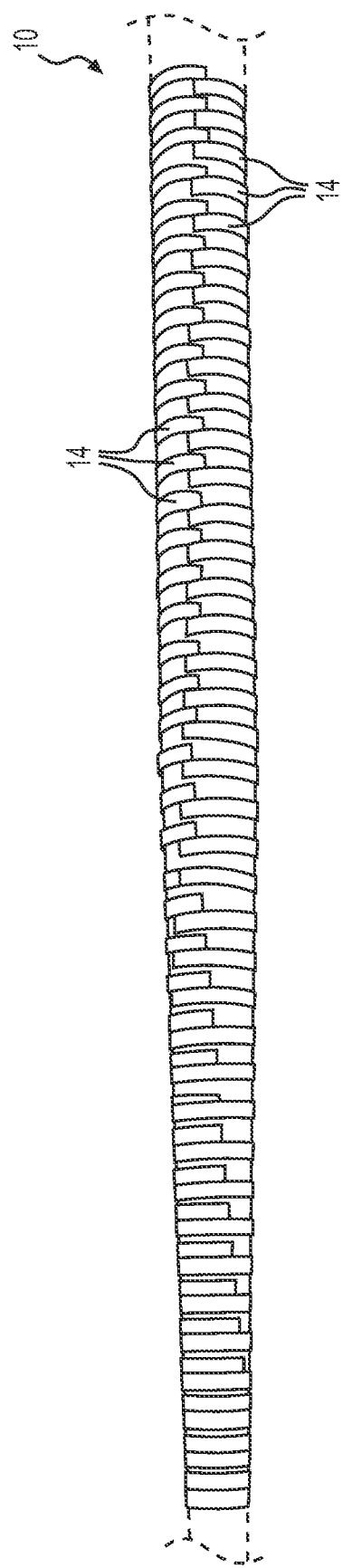

FIGS. 8-11 depict the example sheath 10 before and during expansion by a tapered dilator. FIGS. 8-10 illustrate a tapered dilator (dashed lines) for the purpose of demonstrating the expansion of the curved arms 14. As illustrated in FIGS. 8 and 9, the curved arms 14 can be seen extending away from the longitudinal spine 12. In FIG. 9, the narrow end of the tapered dilator is positioned at the distal end of the sheath 10 (left side of the figure) and the curved arms 16 are shown to extend further around the diameter of the sheath 10 such that their ends can be seen adjacent the longitudinal spine 12. FIGS. 10 and 11 show the opposite side of the expandable sheath 10 with only the curved arms 14 visible. In FIG. 10, only the curved arms 14 at the proximal end (right side of the figure) are being expanded by the dilator. FIG. 11 shows the expandable sheath 10 fully positioned over the tapered dilator. Moving from left to right within FIGS. 10 and 11, the curved arms 14 are expanded to progressively wider diameters, such that their ends move farther and farther from the adjacent longitudinal spine 12 (not shown) and closer to each other (as best seen on the far right side of FIG. 11).

Figure 12:
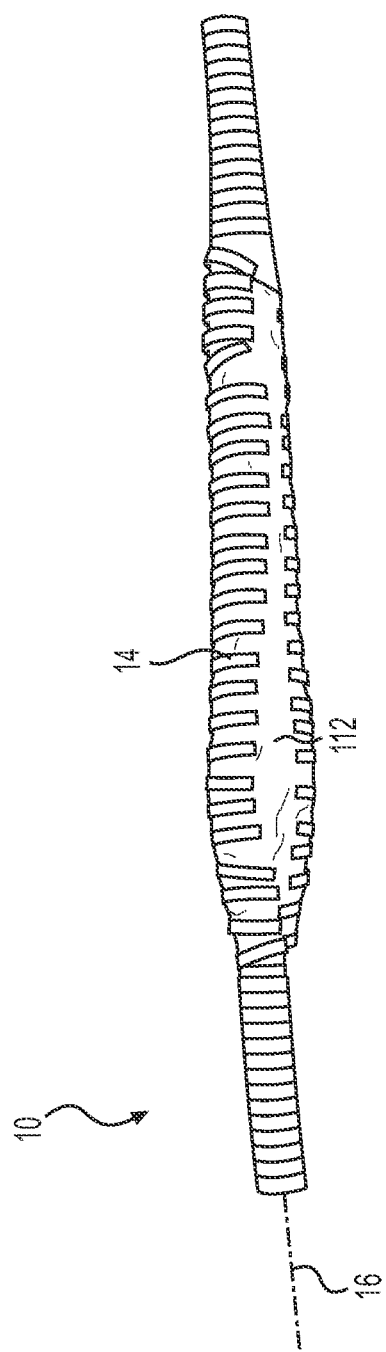
FIG. 12 shows the example sheath of FIG. 8 with a prosthetic device causing radial expansion of the curved arms.

FIG. 12 shows an example prosthetic device 112 being delivered through an expandable sheath 10. The curved arms 14 at the distal end (far left of the figure) have not yet been expanded by the prosthetic device. As illustrated in FIG. 12, the prosthetic device has already passed the curved arms 14 at the proximal end (far right of the figure), demonstrating that the curved arms 14 return to a non-expanded state after the passage of the prosthetic device. For visualization purposes, the sheath shown in FIG. 12 does not have an elastic polymer tubing 50 over the layers (as described in more detail below). However, an elastic polymer tubing 50 could be included to urge the curved arms 14 to return to their original position after passage of the prosthetic device.

Figure 13:
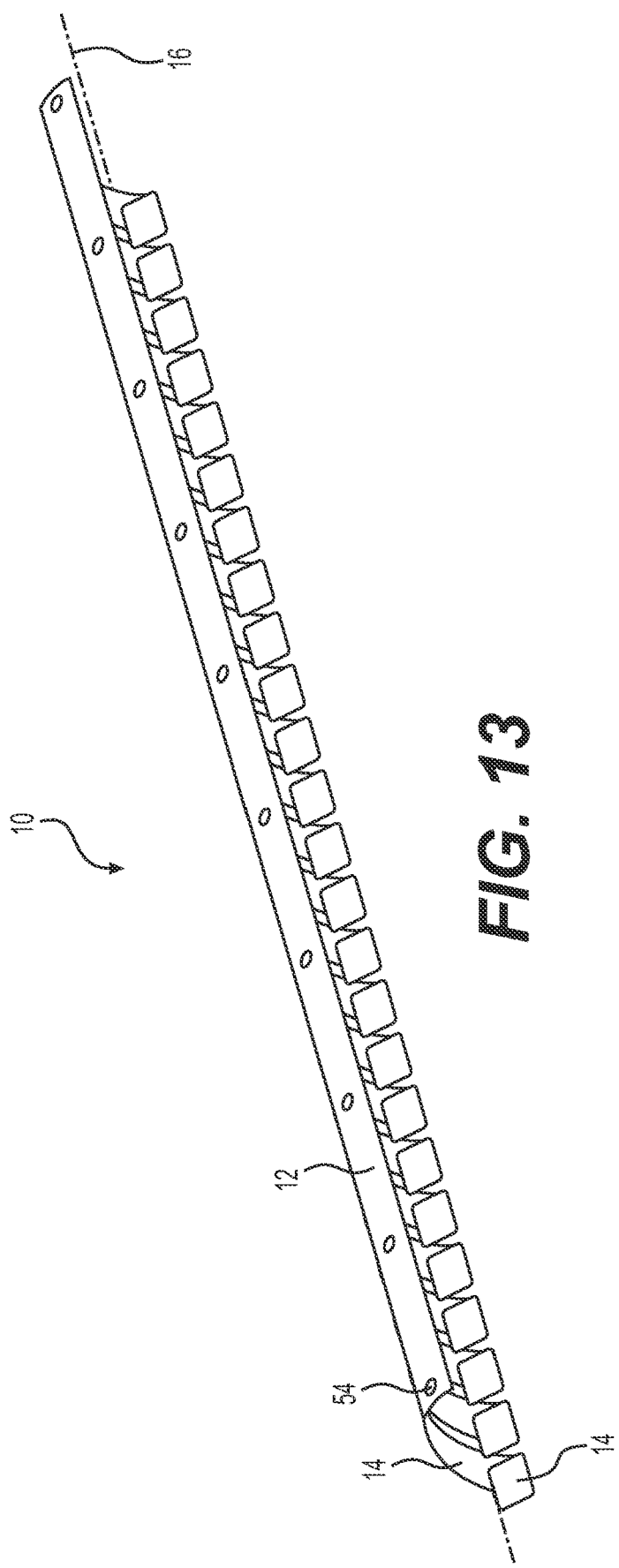
FIG. 13 shows a perspective view of an example sheath having curved arms that extend from the longitudinal spine at an angle.
Figure 14:
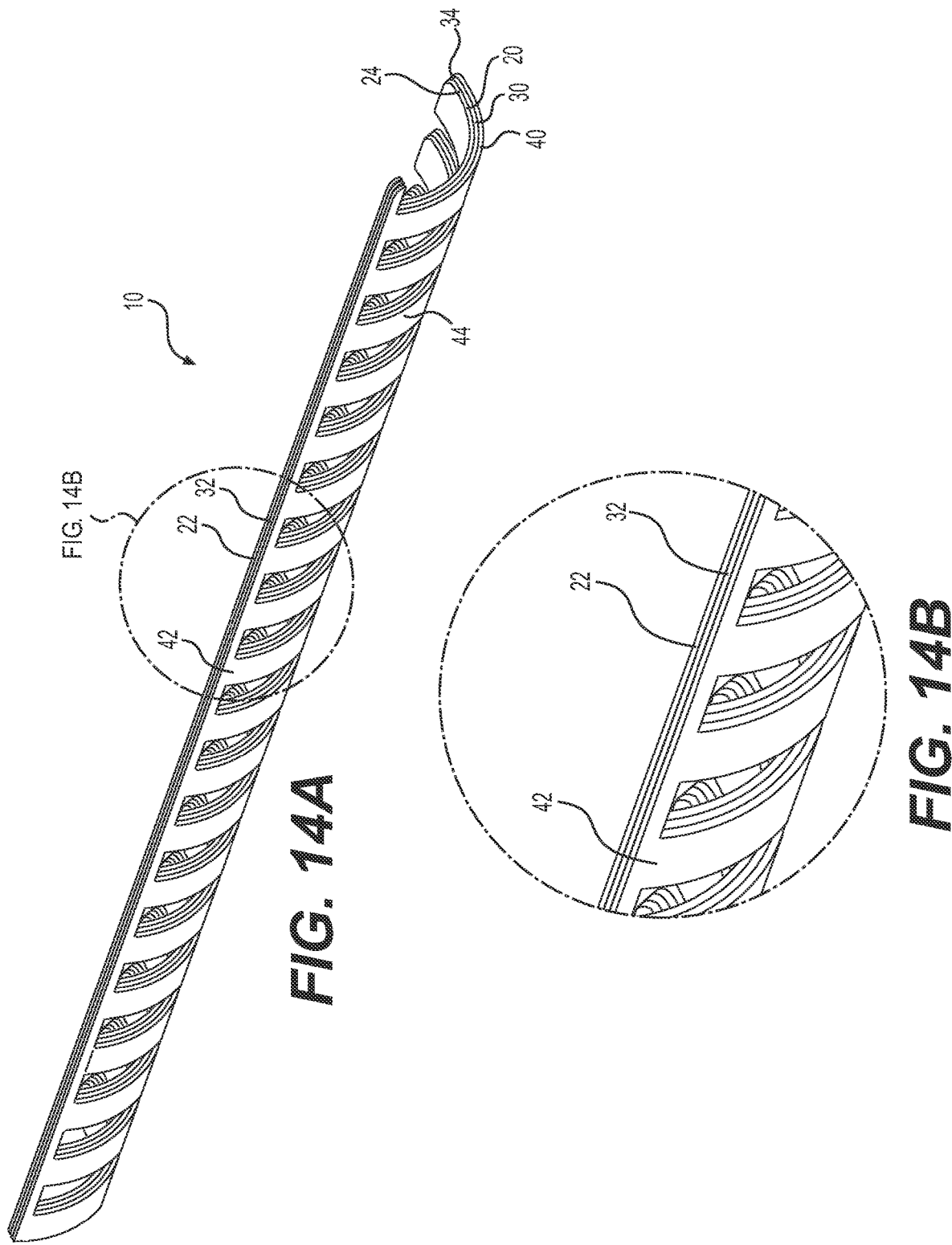
FIG. 14A shows a perspective view of the example sheath of FIG. 13 with the curved arms in the expanded position.
FIG. 14B shows a magnified view of a portion of FIG. 14A.

FIGS. 13-14 illustrate an example sheath 10 having curved arms 14 that extend from the longitudinal spine 12 at an angle. In contrast to the embodiment of FIG. 2, where each curved arm 14 extends at a right angle from the side of the longitudinally extending spine 12, the sheath 10 depicted in FIGS. 13-14 has curved arms 14 extend from the longitudinal spine 12 at an angle other than 90-degrees. The curved arms 14 in the example sheath 10 are also generally longer than the curved arms 14 depicted in the embodiment of FIG. 2. Because the curved arms 14 are longer, they can be opened to a larger expanded diameter and with less resistance. Also, because there are fewer arms in general, there are fewer edges to generate friction with a passing device. This can be advantageous in certain applications where the expanded diameter of the sheath 10 is more than double the non-expanded diameter. By providing a sheath with a larger expanded diameter, the working range of the sheath 10 is increased. The angled arms 14 also provide for greater sensitivity to turns and angles within the vessel. FIG. 13 shows the expandable sheath 10 having angled curved arms 14 in the non-expanded position. FIG. 14A shows the layered curved arms 24, 34, 44 in the expanded position, for example, as if expanded to allow passage of a prosthetic device. FIG. 14B shows a magnified view of FIG. 14A. In the embodiment shown, the arms 14 extend from the spine 12 at an angle of about 45-degrees (measured relative to the longitudinal axis of the sheath 10 and/or longitudinally extending side of the spine 12 and the side edge the curved arm 14). However, it is possible for the curved arms 14 to extend from a single side of the spine 12 at a variety of angles, less than and including 90-degrees. Likewise, the curved arms 14 of the depicted embodiment extend from 270 to 360-degrees around the longitudinal axis 16, but could be designed to curve around the longitudinal axis 16 to a lesser extent. In some embodiments, the curved arms 14 can return to their original position due to the shape memory property of the starting material. Alternatively or in addition, the various layers 20, 30, 40 of the sheath 10 can be partially encapsulated in an elastic polymer tubing 50, as explained in more detail below with respect to FIG. 20. The elastic polymer tubing 50 facilitates the return of the curved arms 14 to their original position by exerting an inward force on the curved arms 14 when they are in their expanded state.

Figure 15:
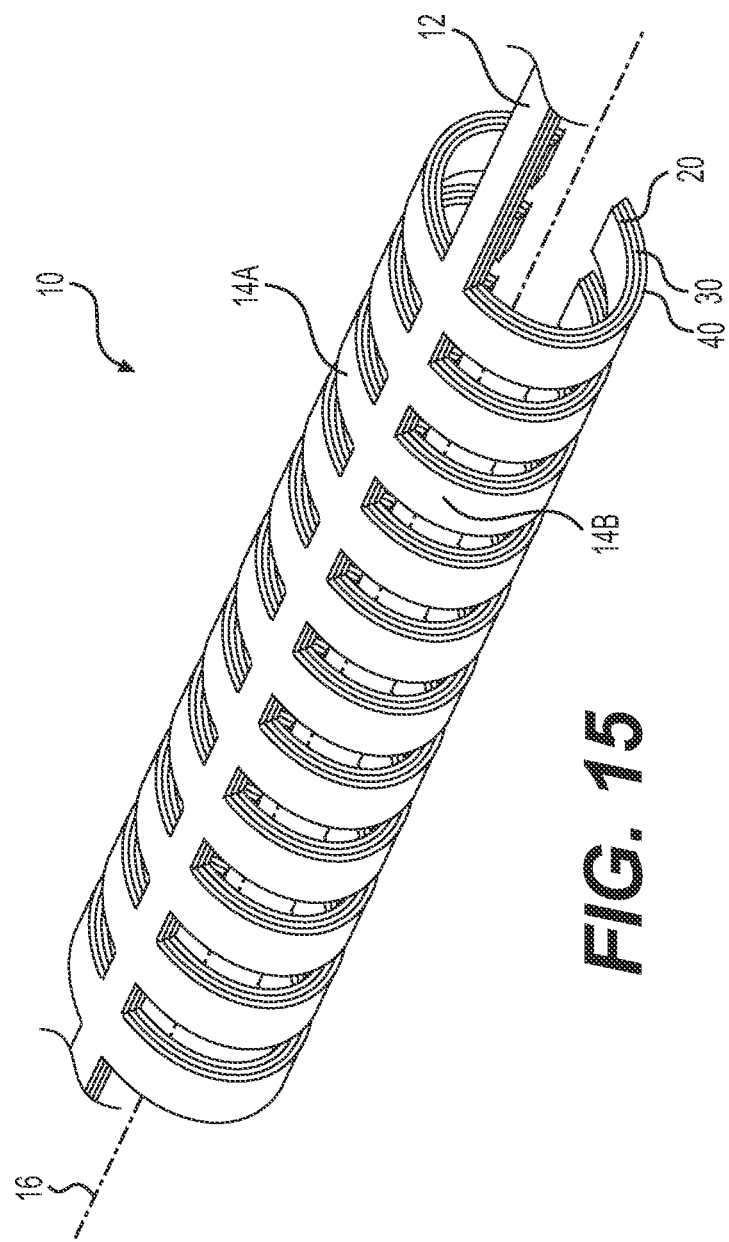
FIG. 15 shows a perspective view of an example sheath having pairs of opposing curved arms extending from the longitudinally extending spine.

In the embodiment shown in FIG. 15, the curved arms 14 extend from the longitudinal spine 12 in directly opposing pairs. For example, as illustrated in FIG. 15, a first curved arm 14A extends from the spine 12 in a first (counterclockwise) direction, directly opposite the spine 12 a corresponding second curved arm 14B extends from the spine 12 in a second (clockwise) direction. The series of opposing curved arms 14 can repeat along the length of the spine 12, creating the appearance of ribs. The curved arms 14 in this embodiment can only extend around the longitudinal axis from 90 to 180-degrees.

Figure 16:
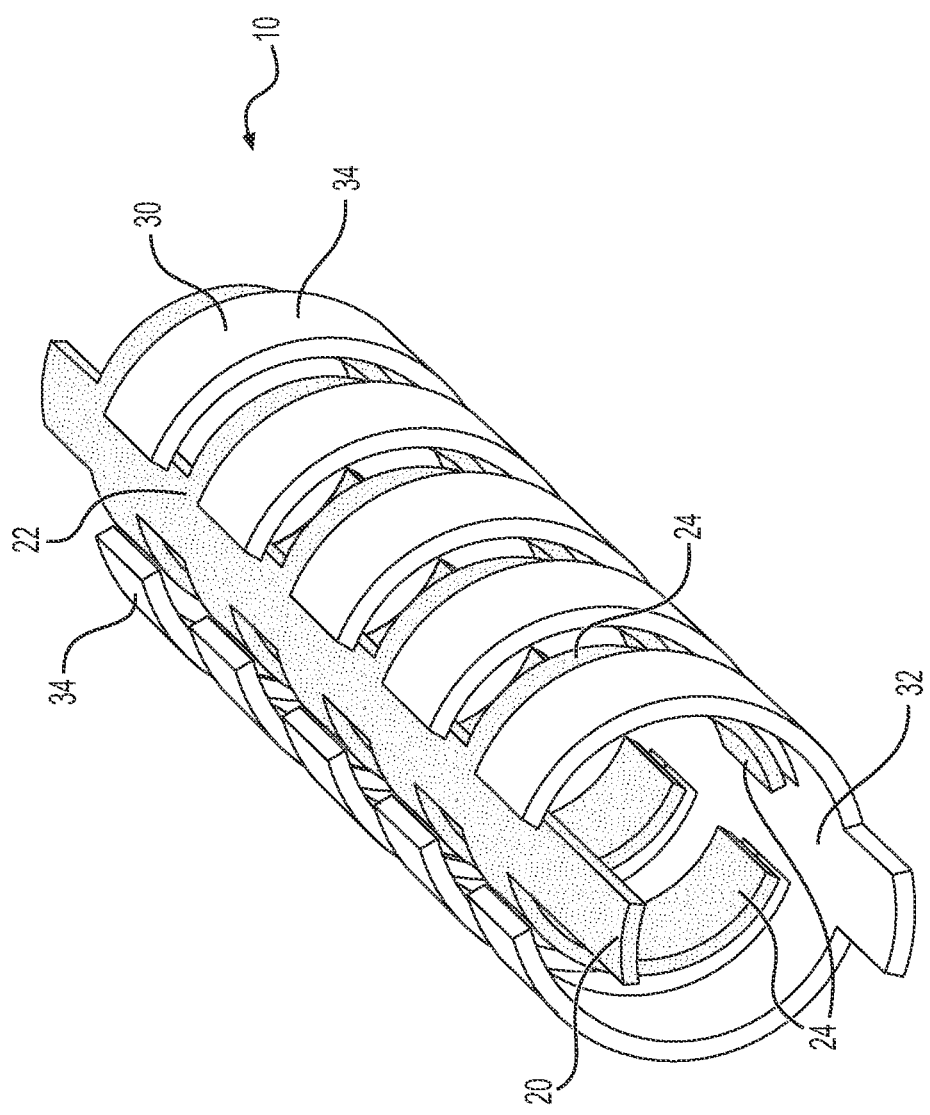
FIG. 16 shows perspective view of an example expandable sheath having longitudinally extending spines circumferentially spaced about the longitudinal axis.

In the embodiment shown in FIG. 16, the two sheath layers 20, 30 are depicted as extending opposite each other such that the spine 22, 32 of each sheath layer extends on opposite sides of the circumference of the sheath 10. Though depicted as separate the layers are coupled together via an elastic polymer tubing 50 (not shown) that extends over/around the opposing layers 20, 30. Similar to the sheath depicted in FIG. 13, the curved arms 24, 34 extend from the longitudinally extending spines 22, 32 in opposing pairs. However, unlike the previous embodiments, the longitudinally extending spines 22, 32 are spaced from each other in the circumferential direction by 180-degrees. Other embodiments can also include various circumferential spacing of the longitudinally extending spines 22, 32. For example, in other embodiments, the longitudinally extending spines 22, 32 can be circumferentially spaced from each other by anywhere from 0 to 180-degrees. To prevent longitudinal slippage between the layers, embodiments with circumferentially spaced longitudinally extending spines 12 can be encapsulated within, at least partially, in elastic polymer tubing 50, such as is shown in FIG. 20. Alternatively, one or more circumferentially extending rings 52 can be placed around the outermost layer 20, 30 and/or the elastic polymer tubing 50.

Some embodiments, such as the one shown in FIG. 17, can include layers 20, 30, 40 that are longitudinally staggered from one another. For example, a curved arm 24 of the first layer 20 can extend into the space between curved arms to a greater extent than the curved arm 34 of the second layer 30, which is positioned above/around it. This reduces the total amount of negative space between the combined or layered sets of curved arms 24, 34, 44. This feature can reduce kinking along the longitudinal axis 16, but can also decrease bendability by increasing the stiffness of the sheath 10. Thus, like the amount of spacing between the curved arms 24, 34, 44, the amount of staggering of the layers can be adapted to suit varying applications.

FIGS. 18-19 show an example expandable sheath 10 including a number of links formed from curved arms 14 that pivot at one end from a common longitudinally-extending axis to allow the sheath 10 to expand and contract during delivery of the prosthetic device. As illustrated in FIGS. 18-19, the curved arms 14 can be coupled to a rod-like spine 12. The spine 12 can be formed by threading a metal wire, cable, thin rod, or other suitable material, through the links. Alternatively, individual curved arms 14 can be coupled to adjacent curved arms 14 via a projection/pivot arm extending from an end surface of each arm 14. For example, the curved arms 14 can include a pin-like projection extending from an end surface of the curved arm 14 and a corresponding opening on an opposite end surface of the curved arm 14. In one example, the projection extending from the distal end surface of a first curved arm 14 is received within an opening provided in the proximal end surface of a next adjacent curved arm 14. The projection is rotatably received within the opening of an adjacent curved arm 14 to allow each of the curved arms 14 to pivot at the projection/opening, thus allowing the sheath 10 to expand/contract.

Returning to the example sheath 10 depicted in FIG. 18A, the curved arms 14 are rotationally coupled at alternating ends to the spine 12. Each curved arm extends circumferentially at least 180-degrees around the longitudinal axis 16 of the sheath 10 in a non-expanded state (FIG. 18A). The curved arms can also be constructed from an elastically resilient material, such as a flexible polymer, such that during delivery of the prosthetic device, the curved arms 14 rotate and/or flex about the spine 12 to facilitate localized expansion of the sheath 10. FIG. 19A illustrates the sheath 10 in an expanded state. The curved arms 14 can alternate in rotational and/or flexing direction along the sheath 10. For example, as provided in FIGS. 18-19, the curved arms 14 rotate/flex from the spine 12 in alternating clockwise/counterclockwise directions along the length of the sheath 10. As illustrated in FIG. 18A, the first curved arm 14A at the proximal end of the sheath 10 extends from the spine 12 in a first (clockwise) direction. The next/adjacent curved arm 14B extends from the spine 12 in a second, opposite (counterclockwise) direction. In another example (not shown), the curved arms 14 are coupled to the spine 12 such that they all rotate/flex from the spine 12 in the same direction, e.g., all of the curved arms 14 may rotate/flex from the spine in a clockwise direction. In another example (not shown), the curved arms 14 are coupled to the spine 12 such that the direction the curved arms 14 rotate/flex from the spine 12 alternate at regular and/or irregular intervals.

Figure 18B:
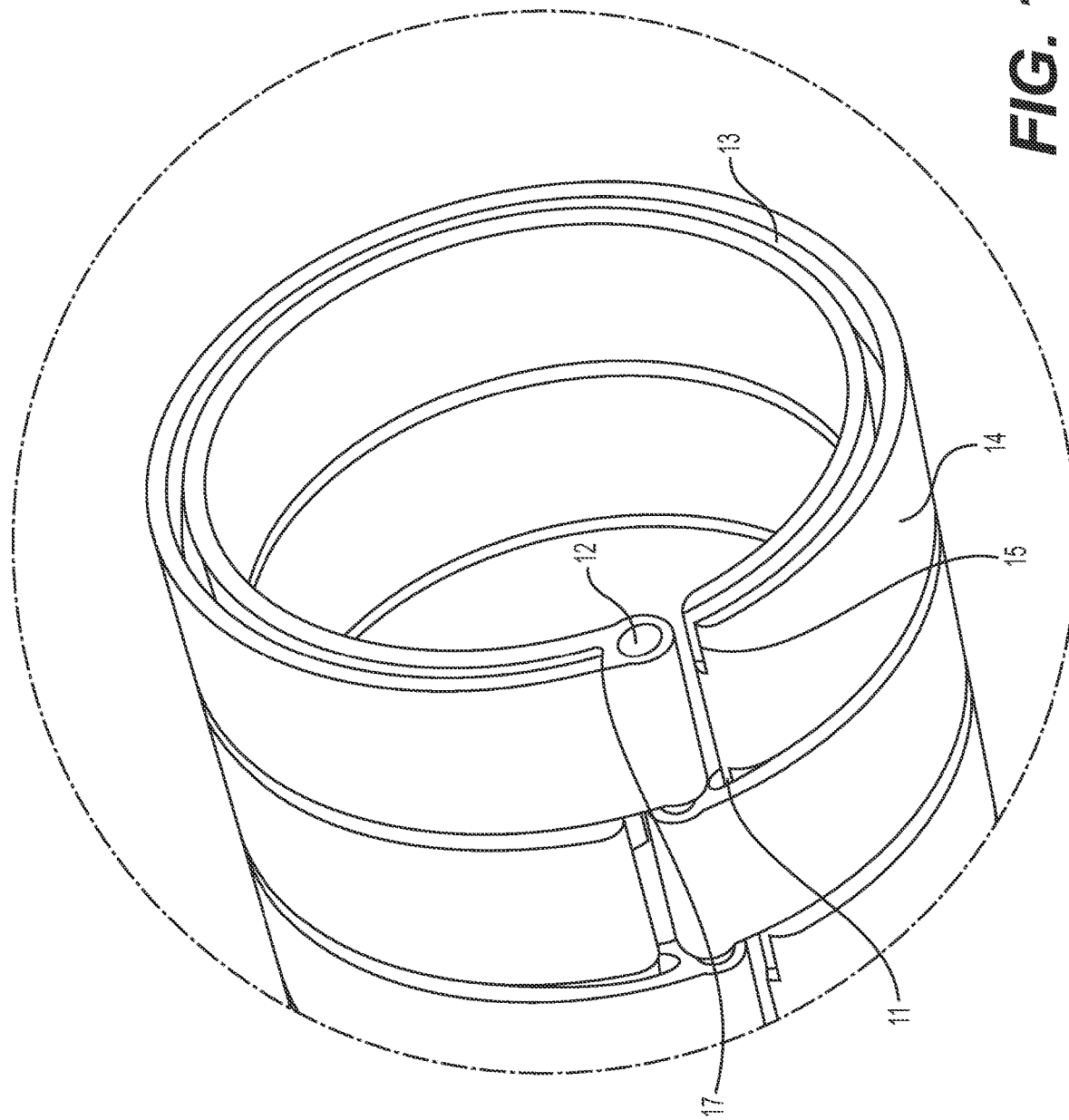
FIG. 18B shows a magnified view of a portion of FIG. 18A.
Figure 19A:
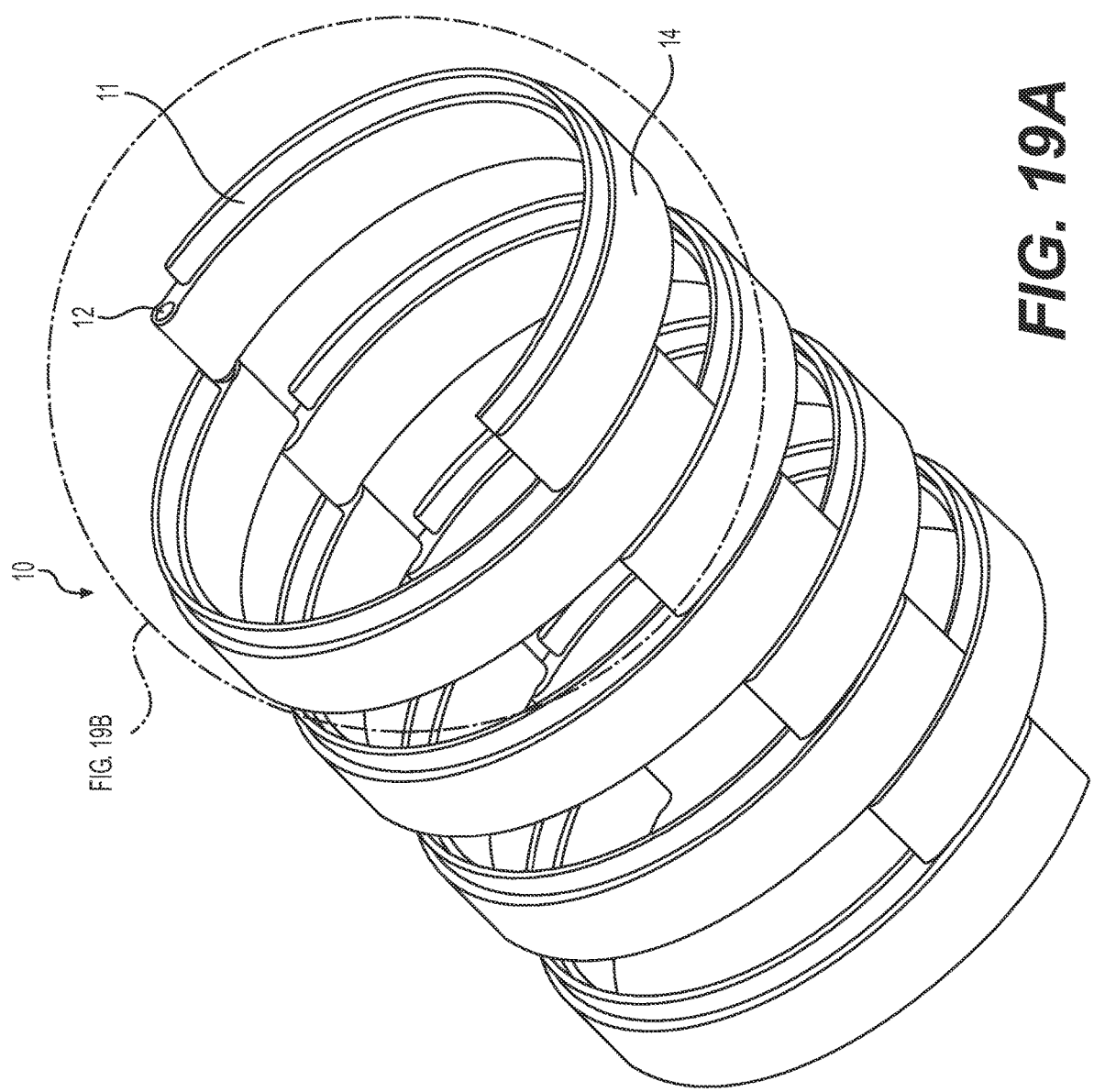
FIG. 19A shows a perspective view of the example sheath of FIG. 18A.
Figure 19B:
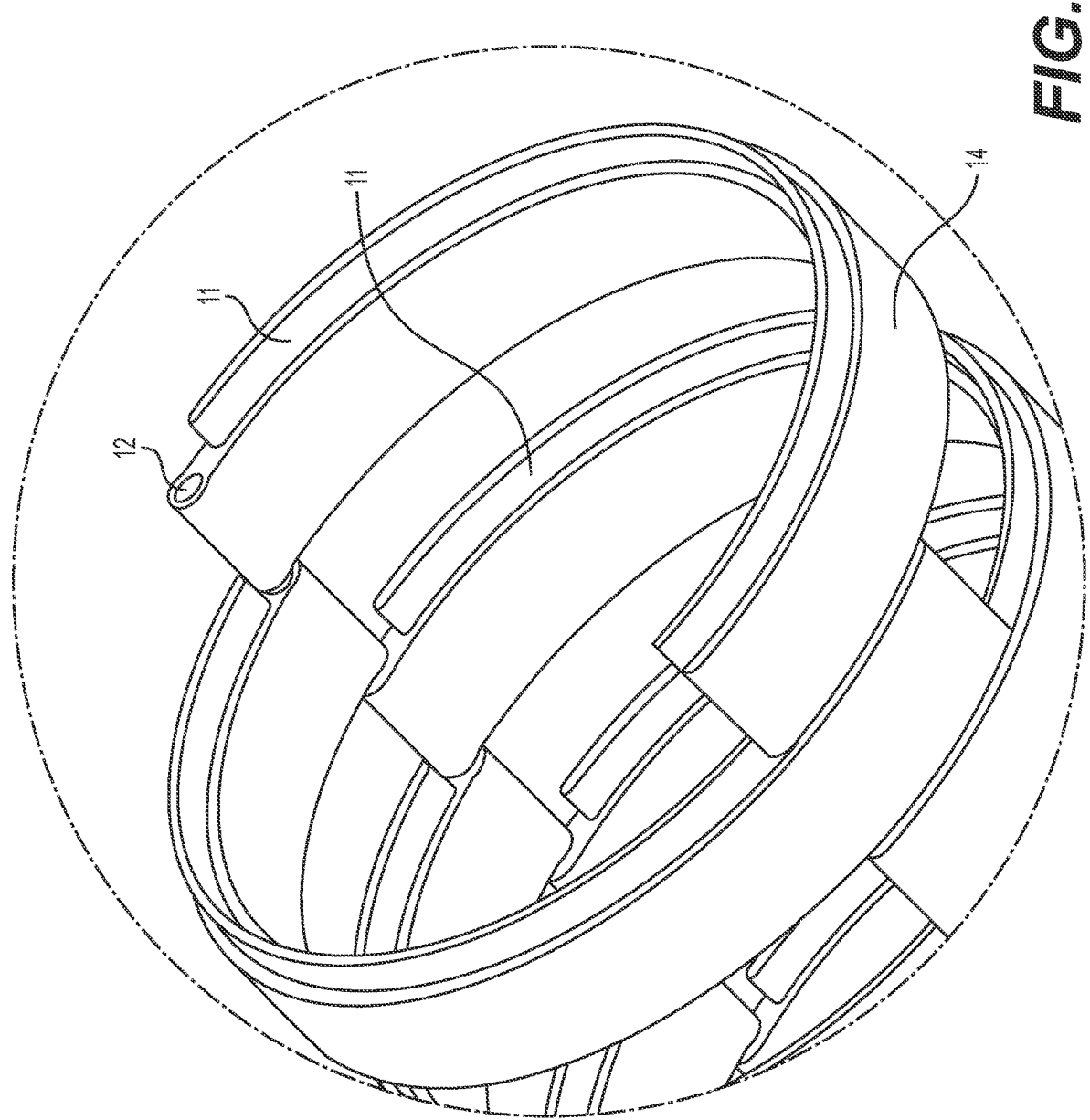
FIG. 19B shows a magnified view of a portion of FIG. 19A.

In the example sheath 10 illustrated in FIGS. 18-19, the curved arms 14 engage or otherwise interlock with an adjacent arm during expansion and contraction of the sheath 10, such that the arms slide against each other. For example, the curved arms 14 can include a projection or ridge 11 sized and configured to engage a corresponding recess/groove 13 provided on an adjacent curved arm 14. An example ridge 11 structure is illustrated in FIGS. 19A and 19B. The ridge 11 extends from an end surface of the curved arm 14 and can define a curved shape generally corresponding to the shape of the curved arm 14 (in cross-section). FIGS. 19A and 19B illustrate the ridge 11 extending from the curved arm 14 along a majority of the length of the curved arm 14, but of course the ridge can extend along less than half of the circumferential length of the curved arm 14. FIGS. 19A and 19B illustrate the ridge 11 extending continuously from the end surface of the curved arm 14. However, the ridge 11 may also extend intermittently from the end of the curved arm 14. That is, the ridge 11 may include a number of ridges 11 that extend from the end of the curved arm 14 with breaks in between.

As illustrated in FIGS. 18A and 18B, the curved arms 14 include a corresponding groove 13 on the opposite side of the curved arm 14 from the ridge 11. The groove 13 is sized and configured to slidingly receive the ridge 11 such that adjacent arms 14 are engaged/interlocked during expansion and contraction of the sheath 10. Similar to the ridge 11, the groove defines a curved shape generally corresponding to the shape of the curved arm 14. The groove 13 includes an opening 15 in the curved arm 14 for receiving the ridge 11. In another example (not shown), the groove 13 may not include a receiving opening but rather define a bounded recess provided on the end surface curved arm 14 such that the ridge 11 of an adjacent curved arm 14 is not released from the groove 13, also ensuring that the curved arms 14 overlap or are always in contact when the sheath 10 is fully expanded. The groove 13 also includes an end surface 17 at the terminating point of the groove 13 within the curved arm 14. The end surface 17 can provide a contact/engagement surface for the ridge 11 to limit further contraction of the sheath 10. That is, engagement between the end surface 17 and an end of the ridge 11 will limit rotational movement of the corresponding arms 14 and contraction of the sheath 10.

The size and shape of the ridge 11, and corresponding grove 13, may vary. For example, the ridge 11 may define a square or curved end surface. The ridge 11 and/or groove 13 can include a tapered surface for facilitating sliding engagement and/or flexation of the curved arms 14. The ridge 11 can be constructed from the same or a different material from the curved arm 14. For example, the ridge 11 can be constructed from a more flexible and/or elastic material than the curved arm 14. Alternatively, the ridge 11 can be constructed from a more rigid/stiff material than the curved arm 14. In another example (not shown), the curved arm 14 does not include a groove. Rather, the ridge 11 slides along an inner or outer surface of the adjacent curved arm 14. In a further example (not shown), the ridge 11 slides within a correspondingly shaped recess provided on the inner or outer surface of the adjacent curved arm 14. By constructing the arms to engage one another and slide against each other, the sheath can withstand high pushing and pulling forces, as adjacent arms are pushed and pulled against each other.

In each of the disclosed embodiments, the sheath 10 can also include an elastic polymer tubing 50 encasing at least part of the length of expandable sheath 10. An example elastic polymer tubing 50 is illustrated in FIGS. 1C and 20. The elastic polymer tubing 50 can extend around the outside of the sheath 10, through the inside of the sheath 10 (between the first (innermost) layer 20 and the longitudinally extending lumen 18), or both. When extending around the outside of the sheath 10, the elastic polymer tubing 50 provides an inwardly directed radial force that serves as a fixation mechanism to prevent longitudinal slippage between the various layers of the expandable sheath 10. The compressive force provided by the elastic polymer tubing 50 can also facilitate the movement of the curved arms 14 back toward the longitudinal axis 16 after their expansion by a passing prosthetic device. Finally, the elastic polymer tubing 50 creates a smooth surface that can minimize damage to the vascular system as the sheath 10 is being positioned and during insertion of the delivery system and implant through the sheath 10. The elastic polymer tubing 50 can be included through the inside of the sheath 10 to protect a passing prosthetic device from damage by the sheath 10 and to reduce friction between the sheath 10 and the device during its passage. The elastic polymer tubing 50 can be formed from a variety of materials including polyether ether ketone (PEEK), polyethylene terephthalate (PET), polyphenylene sulfide (PPS), and composite materials reinforced by carbon or glass fibers. Preferably, the elastic polymer tubing 50 will be formed of biocompatible, anti-clotting materials.

In some embodiments, the expandable sheath 10 can be constructed of a nitinol starting material. The nitinol material can be used for its super elastic properties, i.e. to bring the curved arms back to starting position after the passing of a prosthetic device. Other starting materials could include materials with high elasticity, polymer materials or stainless steel that has been treated to increase elasticity. Treatments to increase the elasticity of the stainless steel could include, for example, thermal treatments, chemical treatments, or mechanical treatments. The individual layers need not be formed from the same starting material.

In some embodiments, the sheath 10 and its individual elements, e.g., the curved arms, the longitudinally extending spines, suture holes, etc., can be laser cut from a tube of the starting material. Alternatively, the material could be cut from a sheet and then bent to form the sheath. The bending could be performed using rolling combined with heat treatment, cold rolling. A shape memory material can also be processed at this stage to set the arms to the nonexpanded state.

As described above, the expandable sheath 10 can be used to deliver, remove, repair, and/or replace a prosthetic device. In one example, the sheath 10 described above can be used to deliver a prosthetic heart valve to a patient. For example, after the sheath is inserted into the body and into the patent's vasculature, a heart valve (in a crimped or compressed state) mounted on the distal end portion of an elongated delivery catheter is inserted into the sheath. Next, the delivery catheter and heart valve can be advanced through the sheath and through the patient's vasculature to the treatment site, where the valve is implanted.

Beyond transcatheter heart valves, the expandable sheath 10 can be useful for other types of minimally invasive surgery, such as any surgery requiring introduction of an apparatus into a subject's vessel. For example, the expandable sheath 10 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. An expandable sheath for delivering a prosthetic device, the expandable sheath comprising:
   a first layer comprising:
   a first longitudinally extending spine extending parallel to a longitudinal axis of the sheath, and
   a first plurality of curved arms attached to and extending away from the first longitudinally extending spine and around the longitudinal axis in a circumferential direction, and
   a second layer positioned around the first layer, the second layer comprising;
   a second longitudinal axis extending between a proximal end of the first layer and a distal end of the second layer,
   a second longitudinally extending spine extending parallel to the longitudinal axis of the sheath, and
   a second plurality of curved arms attached to and extending away from the second longitudinally extending spine and around the longitudinal axis, the second plurality of curved arms at least partially overlaying the first plurality of curved arms,
   wherein longitudinal motion is restricted between the first layer and the second layer, and
   wherein the second plurality of curved arms are configured to slide circumferentially along the first plurality of curved arms.

2. The expandable sheath of claim 1, wherein the first plurality of curved arms are elastically resilient and configured to move away from the longitudinal axis when exposed to a radially outwardly directed force and to move back toward the longitudinal axis upon release of the force,
   wherein the second plurality of curved arms are elastically resilient and configured to move away from the longitudinal axis when exposed to the radially outwardly directed force and to move back toward the longitudinal axis upon release of the force.

3. The expandable sheath of claim 1, wherein the second plurality of curved arms fully overlays the first plurality of curved arms when the sheath is in both an expanded and unexpanded configuration.

4. The expandable sheath of claim 1, wherein the first plurality of curved arms and the second plurality of curved arms extend from their corresponding longitudinally extending spines in alternating directions moving along the longitudinal axis of the sheath.

5. The expandable sheath of claim 1, wherein the first and second plurality of curved arms are rotationally coupled to their corresponding first and second longitudinally extending spine,
   wherein the first plurality of curved arms extend in a first direction about the longitudinal axis of the sheath and the second plurality of curved arms extend in a second, opposite, direction about the longitudinal axis of the sheath,
   wherein individual curved arms of the first plurality of curved arms are arranged alternatively with individual curved arms of the second plurality of curved arms along a length of the expandable sheath.

6. The expandable sheath of claim 5, wherein individual curved arms of the first plurality of curved arms are coupled to individual arms of the second plurality of curved arms are coupled at their corresponding first and second longitudinally extending spine.

7. The expandable sheath of claim 1, wherein each curved arm extends circumferentially more than 270 degrees around the longitudinal axis.

8. The expandable sheath of claim 1, wherein each curved arm extends at a right angle from a side of the corresponding longitudinally extending spine.

9. The expandable sheath of claim 8, wherein the first and second longitudinally extending spines are circumferentially spaced from each other,
   wherein the first and second longitudinally extending spines are circumferentially spaced from each other by about 180-degrees.

10. The expandable sheath of claim 1, wherein each of the first and second plurality of curved arms extend at an acute angle from a side of the corresponding longitudinally extending spine.

11. The expandable sheath of claim 10, wherein each of the curved arms extend at a 45-degree angle from the side of the corresponding longitudinally extending spine.

12. The expandable sheath of claim 1, wherein the curved arms extend from the corresponding longitudinally extending spines in opposing pairs moving along the longitudinal axis,
    wherein each curved arm extends between 90 and 180 degrees circumferentially around the longitudinal axis.

13. An expandable sheath comprising:
    a plurality of curved arms rotationally coupled at their proximal end along a spine, the spine extending parallel to a central longitudinal axis of the sheath, each of the plurality of curved arms including a ridge projecting from an end surface of the curved arm and a correspondingly shaped groove provided in an opposite end surface of the curved arm, such that a ridge of a first curved arm of the plurality of curved arms is received within and slidingly engages the groove of an adjacent curved arm;
    wherein the plurality of curved arms define a longitudinally extending lumen; and
    wherein the plurality of curved arms move away from the central longitudinal axis of the sheath to an expanded state when exposed to a radially outwardly directed force, and the plurality of curved arms move toward the central longitudinal axis upon release of the force.

14. The expandable sheath of claim 13, wherein the plurality of curved arms slidingly engage along the ridge and projection of adjacent ones of the plurality of curved arms during movement to and from the expanded state.

15. The expandable sheath of claim 13, wherein the ridge projects from the end surface along a majority of a circumferential length of the corresponding curved arm.

16. The expandable sheath of claim 13, wherein the ridge has a thickness less than a thickness of the corresponding curved arm.

17. The expandable sheath of claim 13, wherein an outer diameter of the ridge is less than an outer diameter of the curved arm such that each of the plurality of curved arms have a corresponding outer diameter.

18. The expandable sheath of claim 13, wherein the first curved arm includes a projection extending from an end surface of the first curved arm, the projection received within an opening provided on an opposite end surface of the adjacent curved arm such that the first and adjacent curved arms are rotationally coupled at the projection, wherein the projection and the opening extend in a direction along the spine.

19. The expandable sheath of claim 13, wherein the first curved arm rotates away from the central longitudinal axis in a first direction towards the expanded state, and the adjacent curved arm rotates away from the central longitudinal axis in a second direction towards the expanded state.

20. The expandable sheath of claim 13, wherein each of the plurality of curved arms extends circumferentially at least 180 degrees around the central longitudinal axis.

* * * * *